(12) United States Patent
Ahern et al.

(10) Patent No.: US 9,549,722 B2
(45) Date of Patent: Jan. 24, 2017

(54) THORACIC ACCESS PORT INCLUDING FOLDABLE ANCHOR

(71) Applicant: Covidien LP, Mansfield, MA (US)

(72) Inventors: David Gregory Ahern, Cambridgeshire (GB); Robin Craig Cocker, Lancashire (GB)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/835,774

(22) Filed: Aug. 26, 2015

(65) Prior Publication Data

US 2015/0366550 A1 Dec. 24, 2015

Related U.S. Application Data

(62) Division of application No. 13/397,896, filed on Feb. 16, 2012, now Pat. No. 9,119,665.

(60) Provisional application No. 61/454,684, filed on Mar. 21, 2011.

(51) Int. Cl.
*A61F 2/44* (2006.01)
*A61B 17/02* (2006.01)
*A61B 17/34* (2006.01)

(52) U.S. Cl.
CPC ....... *A61B 17/0218* (2013.01); *A61B 17/3423* (2013.01); *A61B 2017/3427* (2013.01); *A61B 2017/3484* (2013.01)

(58) Field of Classification Search
CPC ................ A61B 17/02; A61B 17/0206; A61B 2017/0256
USPC ................................................ 600/201–225
See application file for complete search history.

(56) References Cited

U.S. PATENT DOCUMENTS

| | | | |
|---|---|---|---|
| 1,780,912 | A | 11/1930 | Gau |
| 1,810,466 | A | 6/1931 | Deutsch |
| 2,313,164 | A | 3/1943 | Nelson |
| 2,541,516 | A | 2/1951 | Ivory et al. |
| 2,812,758 | A | 11/1957 | Blumenschein |
| 3,782,370 | A | 1/1974 | McDonald |
| 3,807,393 | A | 4/1974 | McDonald |

(Continued)

FOREIGN PATENT DOCUMENTS

| | | |
|---|---|---|
| DE | 10001695 A1 | 2/2001 |
| DE | 102009014527 A1 | 9/2010 |

(Continued)

OTHER PUBLICATIONS

EP Search Report EP 12160423.5 dated Jun. 25, 2012.

(Continued)

*Primary Examiner* — Matthew Lawson

(57) ABSTRACT

A surgical access device includes a body having a first member and a second member relatively movable between open and closed configurations. Each member is positionable within an opening in tissue to provide access to an interior space of a patient. Each member includes a top surface, a bottom surface, a leading end, and a trailing end. The top surfaces are positioned in close cooperative alignment when the first and second members are in the closed configuration. The trailing ends are positioned in close cooperative alignment when the first and second members are in the open configuration. In the open position, the first and second members define a passage therethrough to permit access to the interior space for passage of a surgical instrument therethrough.

18 Claims, 9 Drawing Sheets

(56) References Cited

U.S. PATENT DOCUMENTS

| | | |
|---|---|---|
| 3,965,890 A | 6/1976 | Gauthier |
| 4,130,113 A | 12/1978 | Graham |
| 4,263,899 A | 4/1981 | Burgin |
| 4,553,537 A | 11/1985 | Rosenberg |
| 5,007,900 A | 4/1991 | Picha et al. |
| 5,052,374 A | 10/1991 | Alvarez-Jacinto |
| 5,080,088 A | 1/1992 | LeVahn |
| 5,125,396 A | 6/1992 | Ray |
| 5,169,387 A | 12/1992 | Kronner |
| 5,231,974 A | 8/1993 | Giglio et al. |
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri et al. |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | de la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | de la Torre et al. |
| 6,033,362 A | 3/2000 | Cohn |
| 6,033,425 A | 3/2000 | Looney et al. |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,473,222 B2 | 1/2009 | Dewey et al. |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 8,403,840 B2 | 3/2013 | Wagner et al. |
| 9,119,665 B2 | 9/2015 | Ahern et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0153927 A1* | 8/2003 | DiPoto ............ A61B 17/0218 606/108 |
| 2003/0191371 A1 | 10/2003 | Smith et al. |
| 2004/0049099 A1 | 3/2004 | Ewers et al. |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2007/0027364 A1 | 2/2007 | Schwer |
| 2007/0038032 A1 | 2/2007 | De Canniere et al. |
| 2007/0073110 A1 | 3/2007 | Larson et al. |
| 2007/0167980 A1 | 7/2007 | Figulla et al. |
| 2008/0132766 A1 | 6/2008 | Dant et al. |

(56) References Cited

U.S. PATENT DOCUMENTS

| | | |
|---|---|---|
| 2008/0234550 A1 | 9/2008 | Hawkes et al. |
| 2009/0105655 A1 | 4/2009 | DeSantis et al. |
| 2009/0204067 A1 | 8/2009 | Abu-Halawa |
| 2009/0265941 A1 | 10/2009 | Kurrus |
| 2009/0299148 A1 | 12/2009 | White et al. |
| 2009/0326469 A1 | 12/2009 | Rockrohr |
| 2010/0168522 A1 | 7/2010 | Wenchell et al. |
| 2010/0210916 A1 | 8/2010 | Hu et al. |
| 2010/0234689 A1 | 9/2010 | Wagner et al. |
| 2010/0234690 A1* | 9/2010 | Joie .................. A61B 17/0206 600/219 |
| 2010/0261970 A1 | 10/2010 | Shelton, IV et al. |
| 2010/0298646 A1 | 11/2010 | Stellon et al. |
| 2011/0021879 A1 | 1/2011 | Hart et al. |
| 2011/0105850 A1 | 5/2011 | Voegele et al. |

FOREIGN PATENT DOCUMENTS

| | | |
|---|---|---|
| EP | 0177177 A2 | 4/1986 |
| EP | 2179699 A1 | 4/2010 |
| EP | 2228014 A1 | 9/2010 |
| EP | 2228024 A1 | 9/2010 |
| EP | 2238931 A1 | 10/2010 |
| EP | 2417922 A1 | 2/2012 |
| EP | 2422725 A2 | 2/2012 |
| EP | 2462883 A1 | 6/2012 |
| GB | 2275420 A | 8/1994 |
| WO | 95/00197 A1 | 1/1995 |
| WO | 95/15715 A1 | 6/1995 |
| WO | 01/08563 A2 | 2/2001 |
| WO | 03/034908 A2 | 5/2003 |
| WO | 2005089655 A1 | 9/2005 |
| WO | 2010042913 A2 | 4/2010 |
| WO | 2010/136805 A1 | 12/2010 |
| WO | 2011/079374 A1 | 7/2011 |

OTHER PUBLICATIONS

EP Search Report EP 11 18 9987 dated Feb. 15, 2012.
EP Search Report EP 12 15 4733 dated Jan. 14, 2014.
EP Search Report EP 11 19 1403 dated Dec. 11, 2013.
European Search Report corresponding to European Patent Application No. 11 25 0163.0, completed on May 26, 2011 and mailed on Jun. 7, 2011; 5 pages.
European Search Report corresponding to European Patent Application No. 11 25 0164.8, completed on May 30, 2011 and mailed on Jun. 8, 2011; 6 pages.
European Search Report corresponding to European Patent Application No. 11 25 0719.9, completed on Nov. 9, 2011 and mailed on Nov. 16, 2011; 7 pages.

* cited by examiner

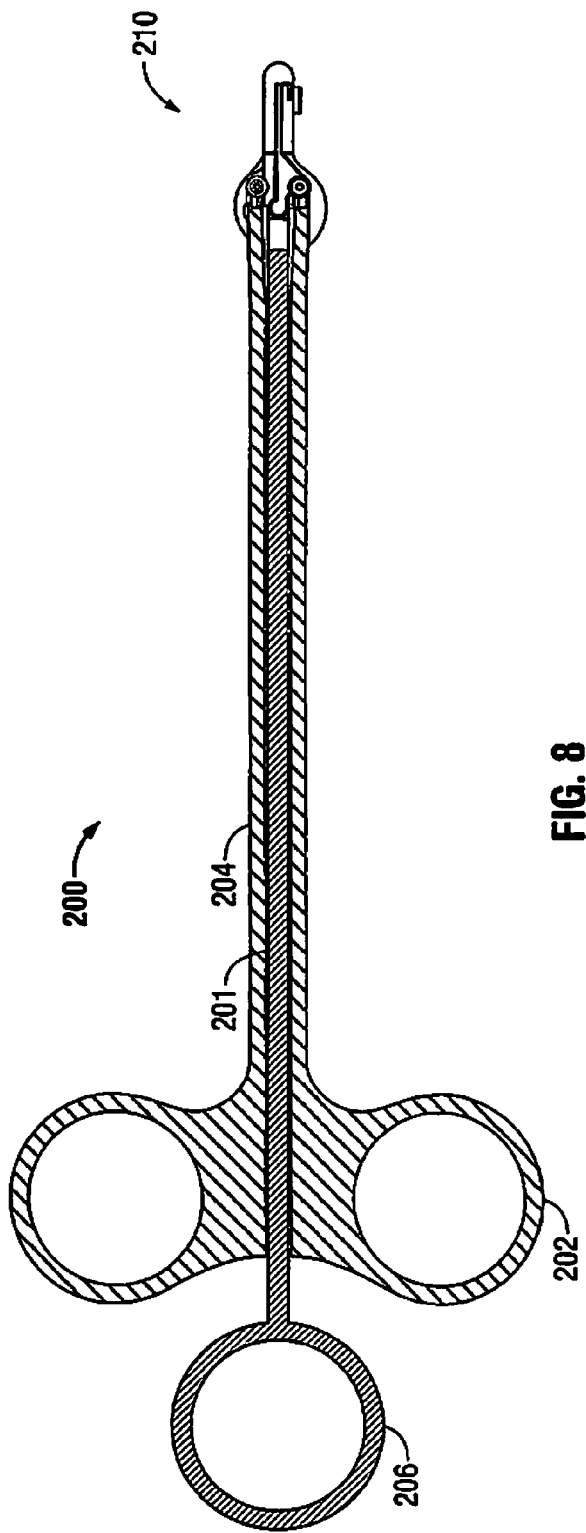
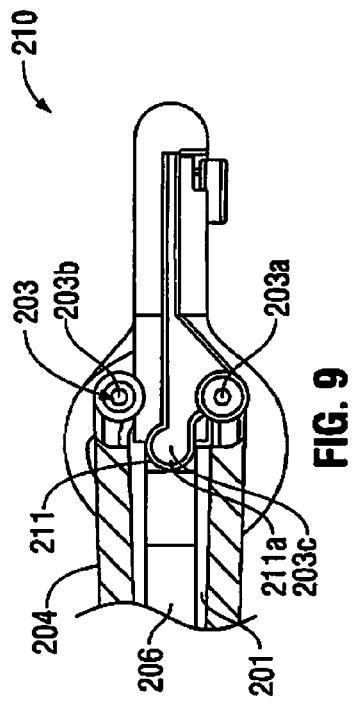
FIG. 8
FIG. 9

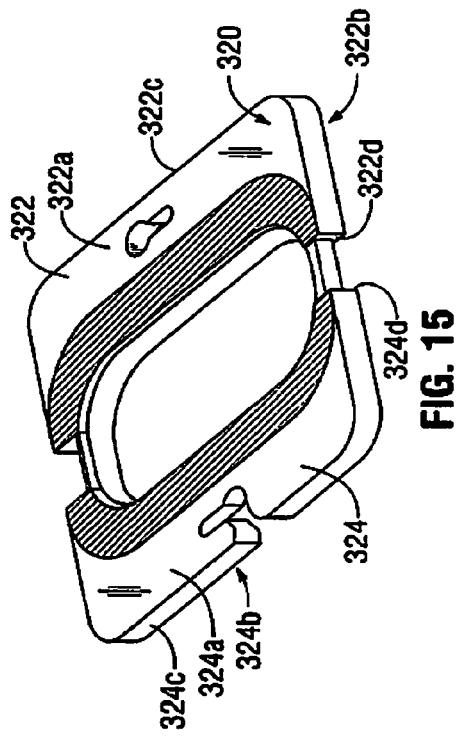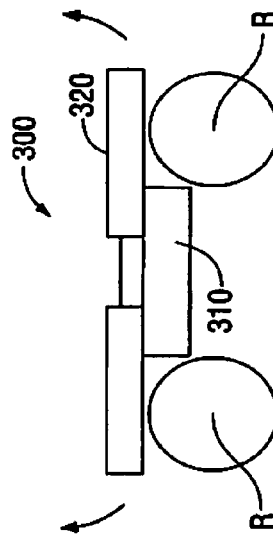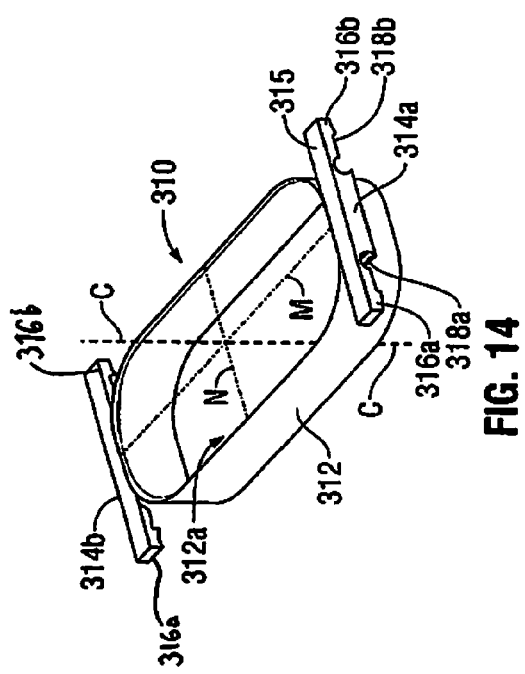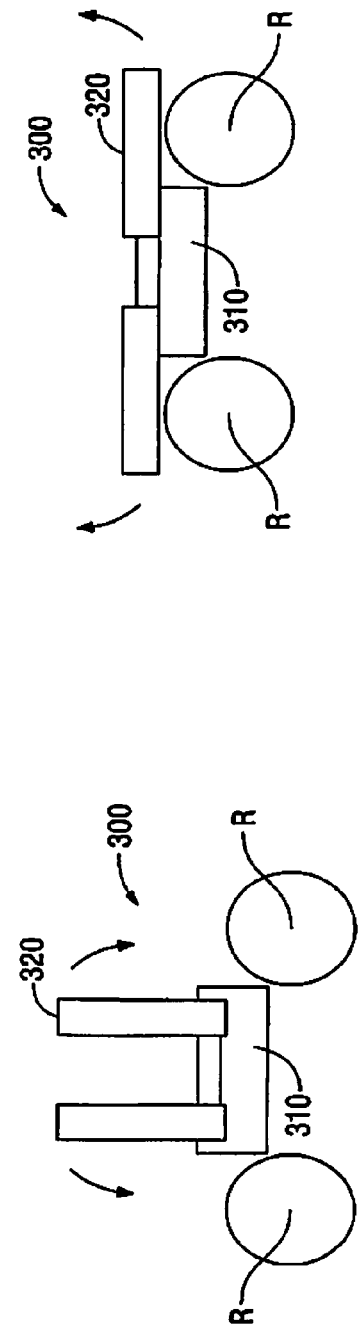
FIG. 14
FIG. 15
FIG. 16
FIG. 17

THORACIC ACCESS PORT INCLUDING FOLDABLE ANCHOR

CROSS-REFERENCE TO RELATED APPLICATIONS

This application is a divisional of U.S. patent application Ser. No. 13/397,896 filed Feb. 16, 2012, which claims benefit of U.S. Provisional Application No. 61/454,684 filed Mar. 21, 2011, and the disclosures of each of the above-identified applications are hereby incorporated by reference in their entirety.

BACKGROUND

1. Technical Field

The present disclosure relates generally to devices and techniques for performing surgical procedures. More particularly, the present disclosure relates to an access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site through the passageway in the access assembly.

In the interests of facilitating visualization, the introduction of certain surgical instruments, and/or the removal of tissue specimens during minimally invasive thoracic procedures, it may be desirable to spread the tissue adjacent the ribs defining the intercostal space and/or the ribs. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for thoracic access ports which minimize post operative patient pain while enabling atraumatic retraction of tissue and which do not restrict access to the body cavity. There also exists a need to facilitate insertion of such thoracic ports into the body cavity.

SUMMARY

According to one aspect of the present disclosure, a surgical access device is provided which includes a body that includes a first member and a second member. Each member includes a top surface, a bottom surface, a leading end, and a trailing end. The first and second members are relatively movable between open and closed configurations and are positionable within an opening in tissue to provide access to an interior space of a patient. The first and second members in the open configuration define a passage therethrough. The passage is dimensioned to permit access to the interior space of the patient for passage of a surgical instrument therethrough.

Preferably, the trailing ends are positioned in close cooperative alignment when the first and second members are in the open configuration and the top surfaces are positioned in close cooperative alignment when the first and second members are in the closed configuration.

In some embodiments, in the open configuration, the leading ends of the first and second members are diametrically opposed and the top and bottom surfaces of the first member are substantially aligned with the top and bottom surfaces of the second member along an axis substantially transverse to a central axis defined through the passage. In some embodiments, in the closed configuration, the leading and trailing ends of the first member are substantially aligned with the leading and trailing ends of the second member and the bottom surfaces of the first and second members are disposed in substantially mirrored relation.

In some embodiments, one or both of the first and second members include one or more flaps extending into the passage.

In some embodiments, one or both of the first and second members define one or more apertures dimensioned to facilitate the positioning of the first and the second members into the open configuration. The apertures can include a first portion and a second portion wherein the first portion is smaller than the second portion. Each of the first and second members can include a surface feature defined along the top surface thereof wherein each respective surface feature can be in contact with the other surface feature when the first and second members are in the closed configuration. One or more of the surface features may include a tapered portion.

In some embodiments, a first arm extends from one of the first and second members and a second arm extends from the other of the first and second members. In such embodiments, the first arm can define a channel dimensioned to receive the second arm such that the first arm and the second arm are engaged in close geometric fit when the first and second members are positioned in the open configuration so that the first and second members are secured in the open configuration.

In some embodiments, one or more cords may be secured to one or both of the first arm and the second arm wherein when the first and second members are secured in the open configuration, the one or more cords are actuable upon the application of a predetermined amount of force to disengage the first and second arms from a close geometric fit so that the first and second members are no longer secured in the open configuration. An opening may be defined within the first arm and/or the second arm through which the one or more cords may be secured.

According to another aspect, a surgical access system is provided and includes a surgical access device and an insertion device. The surgical access device includes a body that includes a first member and a second member. Each member is movable between open and closed configurations and is positionable within an opening in tissue to provide access to an internal space of a patient. The first and second members in the open configuration define a passage therethrough. The passage is dimensioned to permit access to the internal space of a patient for passage of a surgical instrument therethrough.

The insertion device includes a housing having a shaft extending from the housing. At least one movable element extends from a distal end of the shaft. An actuator is operably coupled to at least one movable element and is operable to move at least one movable element between first and second positions. The at least one movable element is releaseably engageable with at least one of the first and second members of the surgical access device such that movement of at least one movable element between the first and second positions repositions the first and second members of the surgical access device between open and closed configurations when at least one movable element is engaged with at least one of the first and second members of the surgical access device.

In some embodiments, the at least one movable element is substantially aligned with a longitudinal axis of the insertion device in the first position and substantially aligned with an axis transverse to the longitudinal axis of the insertion device in the second position.

The passage defined through the first and second members in the open configuration may in some embodiments be substantially elliptical and define a plane including major and minor axes. In some embodiments, when the one or more movable elements are positioned in the second position, the one or more movable elements are prevented from crossing the plane defined by a substantially elliptical passage of the surgical access device when the one or more movable elements are not substantially aligned with the major axis defined by the substantially elliptical passage of the surgical access device.

In some embodiments, each member includes a top surface, a bottom surface, a leading end, and a trailing end, wherein the top surfaces are positioned in close cooperative alignment when the first and second members are in the closed configuration and the trailing ends are positioned in close cooperative alignment when the first and second members are in the open configuration and in the closed configuration.

In some embodiments, the first member and/or the second member of the surgical access device define one or more apertures and the one or more movable elements of the insertion device include one or more protuberances extending therefrom wherein the one or more apertures and the one or more protuberances are releasably engagable with each other. The one or more apertures can have a first portion and a second portion wherein the first portion is smaller than the second portion such that the one or more protuberances of the one or more movable elements are dimensioned to engage the smaller portion of the one or more apertures in a tight geometric fit and the larger portion in a loose geometric fit such that the one or more protuberances remain substantially secured to the smaller portion of the one or more apertures when engaged therewith and are substantially freely movable relative to the larger portion of the one or more apertures when engaged therewith.

According to yet another aspect, the present disclosure is directed to a method of accessing an internal surgical work site relative to an intercostal space defined between a patient's ribs. The method includes the step of providing a surgical access device including a body having a first member and a second member, each member including a top surface, a bottom surface, a leading end, and a trailing end. The method includes providing an insertion device including a housing having a shaft extending from the housing, at least one movable element extending from a distal end of the shaft, and an actuator operably coupled to the at least one movable element and operable to move the at least one movable element between first and second positions. The method includes the steps of coupling the at least one movable element to one or both of the first and second members, selectively positioning the first and second members between a closed configuration, where the top surfaces of first and second members are positioned in close cooperative alignment, and an open configuration. The method further includes positioning the first and second members relative to the intercostal space with the insertion device and uncoupling the at least one movable element from at least one of the first and second members.

The method may include the step of removing the surgical access device from the intercostal space by pulling one or more cords operably coupled to the surgical access device. The method may include the step of rotating the insertion device after uncoupling the one or more movable elements of the insertion device from the first and second members of the surgical access device in order to permit removal of the insertion device through a passage defined through the first and second members of the surgical access device.

BRIEF DESCRIPTION OF THE DRAWINGS

Various exemplary embodiments of the present disclosure are described herein below with reference to the drawings, wherein:

FIG. 8 is a side, cross-sectional view of the insertion device of the surgical access assembly of FIGS. 1 and 2, the insertion device shown in the closed configuration;

FIG. 9 is an enlarged, side, cross-sectional view of the distal end of the insertion device of the surgical access assembly of FIGS. 1 and 2, the distal end of the insertion device shown in the closed configuration;

FIG. 14 is a perspective view of the base of the surgical access device of FIG. 13;

FIG. 15 is a perspective view of the body of the surgical access device of FIG. 13;

FIG. 16 is a front illustrative view of the surgical access device of FIG. 13 shown in the closed configuration;

FIG. 17 is front illustrative view of the surgical access device of FIG. 13 shown in the open configuration.

DETAILED DESCRIPTION OF THE EMBODIMENTS

Figure 2:
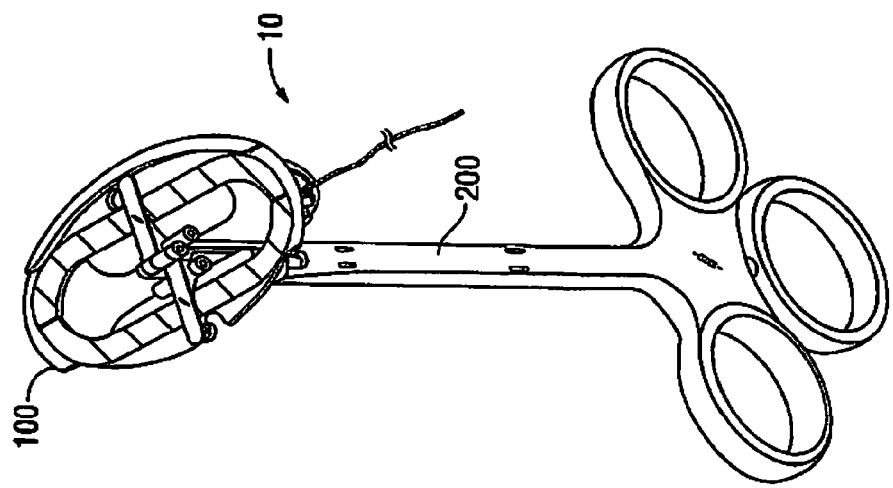
FIG. 2 is a perspective view of the inner member of the surgical access assembly of FIG. 1 shown in an open configuration on the insertion device with the membrane removed for clarity.

Various embodiments of the presently disclosed access assembly, and methods of using the same, will now be described in detail with reference to the drawings wherein like references numerals identify similar or identical elements. In the drawings, and in the following description, the term "proximal" should be understood as referring to the end of the access assembly, or component thereof, that is closer to the clinician during proper use, while the term "distal" should be understood as referring to the end that is farther from the clinician, as is traditional and conventional in the art. Additionally, use of the term "tissue" herein below should be understood to encompass both the patient's ribs, and any surrounding tissues. It should also be understood that the term "minimally invasive procedure" is intended to include surgical procedures through small openings/incisions performed within a confined space such as the thoracic cavity or abdominal cavity.

Figure 1:
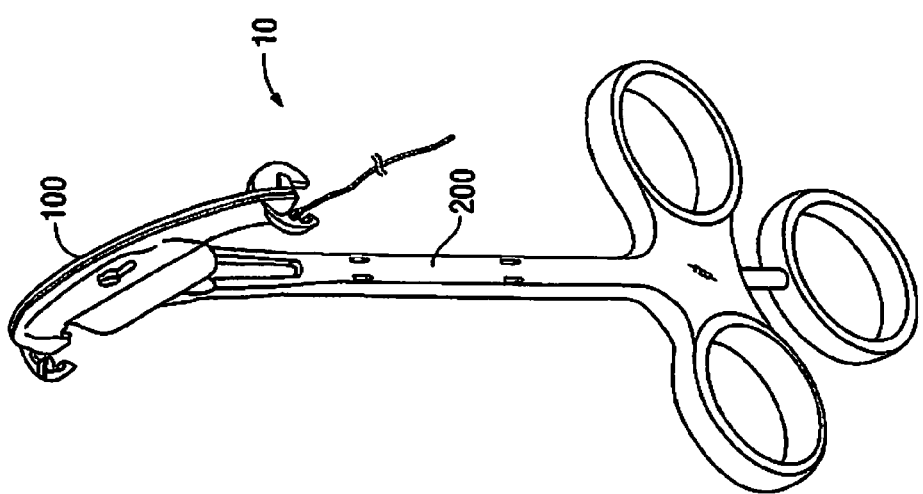
FIG. 1 is a perspective view of the inner member of a surgical access assembly in accordance with the present disclosure shown in a closed configuration mounted to an insertion device with the membrane removed for clarity.
Figure 3:
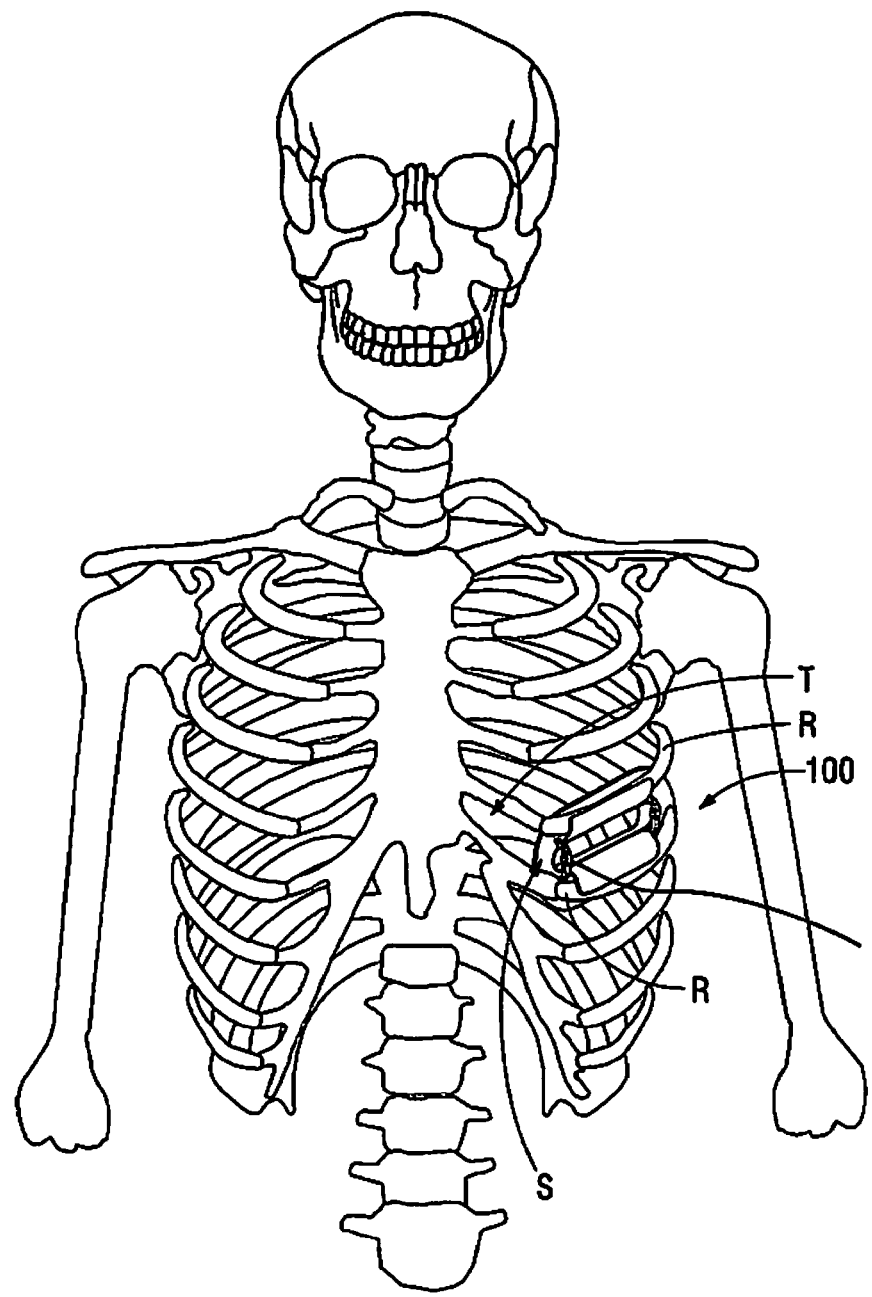
FIG. 3 is a front view illustrating a patient's skeletal structure with one embodiment of the presently disclosed surgical access device of the presently disclosed surgical access assembly of FIGS. 1 and 2 positioned within the intercostal space defined between adjacent ribs.

Referring now to the drawings, FIGS. 1-12 illustrate one embodiment of the presently disclosed surgical access assembly that is generally referred to by reference numeral 10, in use for a minimally invasive thoracic surgical procedure. The various components of the surgical access assembly 10 may be formed from any suitable biocompatible material, including, but not limited to, polymeric materials. With particular reference to FIGS. 1-2, the surgical access assembly 10 includes a surgical access device 100 and an insertion device 200. The surgical access device (access port) 100 is depicted as a thoracic access device configured and dimensioned for insertion by the insertion device 200 into the intercostal space "S" (FIG. 3), thereby providing on access port for the insertion of one or more surgical instruments (not shown) therethrough for manipulation within the thoracic cavity "T" (FIG. 3). The intercostal space "S" is located between a patient's adjacent ribs "R" through an opening or incision in tissue. A membrane (not shown in FIGS. 1 and 2) as described below preferably also forms part of the access device 100.

Figure 5:
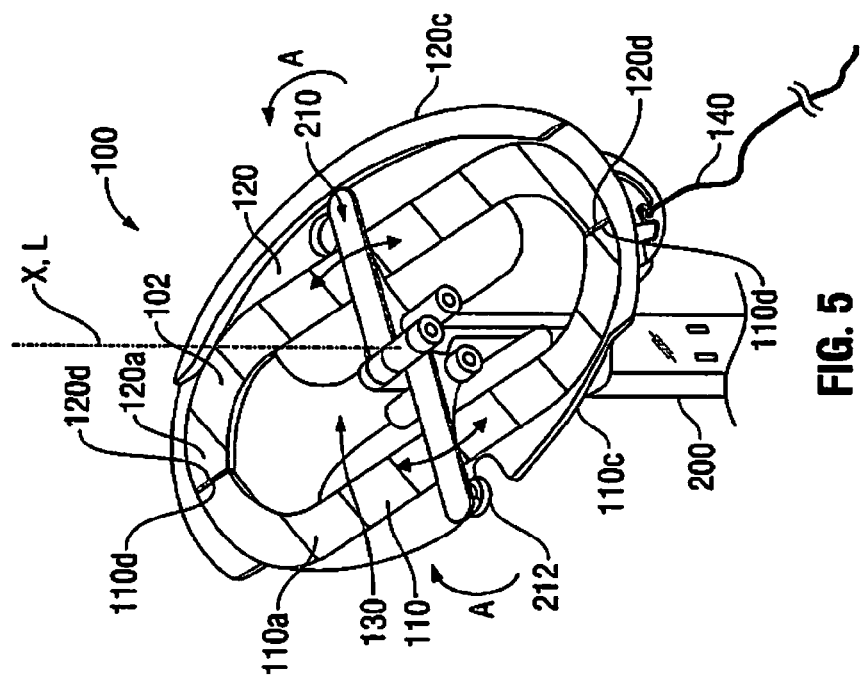
FIG. 5 is an enlarged, perspective view of the distal end of the surgical access assembly of FIGS. 1 and 2.
Figure 4:
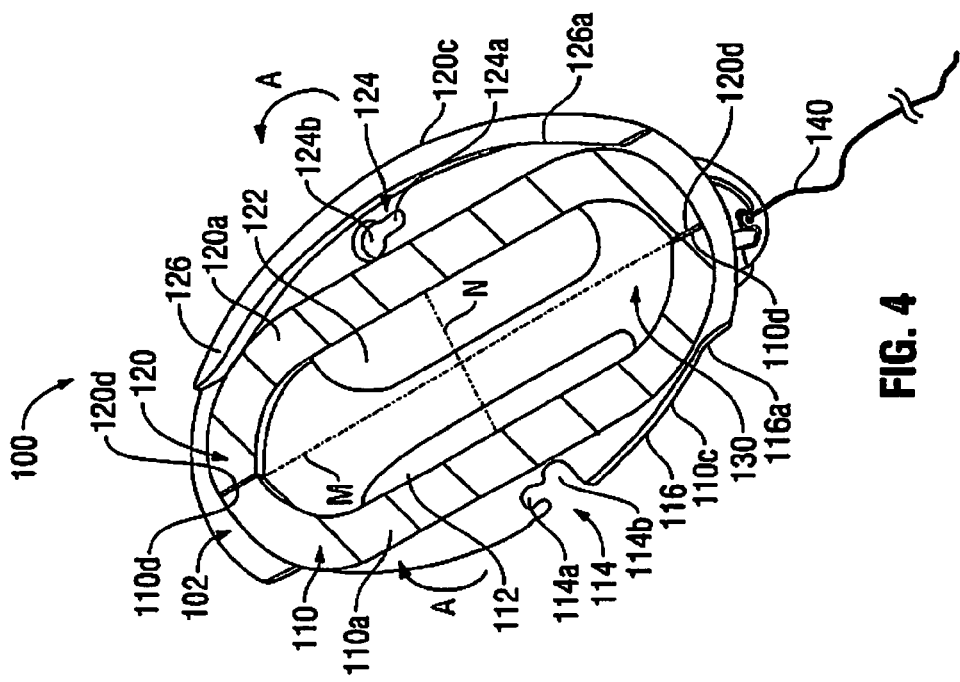
FIG. 4 is an enlarged, perspective view of the surgical access device of FIG. 1 shown in the open configuration.
Figure 6:
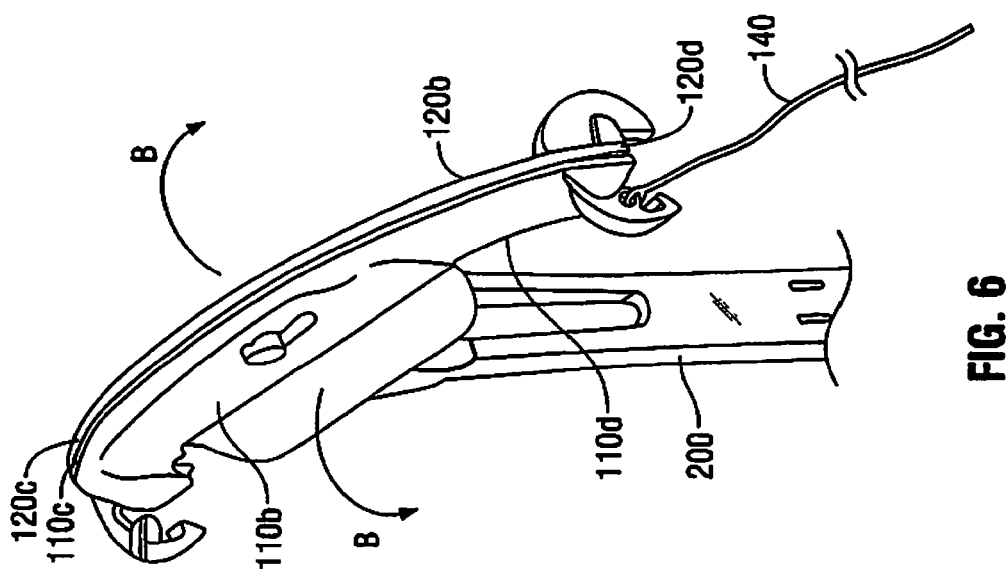
FIG. 6 is an enlarged, perspective view of the distal end of the surgical access assembly of FIGS. 1 and 2 shown in the closed configuration.

With reference to FIGS. 4-7, the surgical access device 100 includes a body 102 that includes a first member 110 and a second member 120. The first member 110 includes a top surface 110a, a bottom surface 110b, a leading end (or outer end or edge) 110c, and a trailing end (or inner end or edge) 110d. The second member 120 includes a top surface 120a, a bottom surface 120b, a leading end (or outer end or edge) 120c, and a trailing end (or inner end or edge) 120d. The first and second members 110, 120 are each movable between open (FIGS. 4 and 5) and closed (FIG. 6) configurations and are positionable within the opening in tissue to provide access to the intercostal space "S" (FIG. 3) defined between a patient's adjacent ribs "R" (FIG. 3). As best shown by the arrows "A" and "B" in FIGS. 4-6, one or both of the first and second members 110, 120 may rotate as the first and second members 110, 120 move between the open and closed configurations. For example, each of the first and second members 110, 120 may rotate from between about 45 degrees to about 135 degrees between the open and closed configurations. Other degrees of rotation are also contemplated. As illustrated in FIGS. 5 and 6, each of the first and second members 110, 120 are shown rotating about 90 degrees between the open and closed configurations. The first and second members 110, 120 define a passage 130 therethrough when positioned in the open configuration. The passage 130 is dimensioned to permit access to the intercostal space "S" (FIG. 3) for passage of one or more surgical instruments into an internal work site of a thoracic cavity "T" (FIG. 3). As best shown in FIG. 4, the passage 130 may be substantially rectangular with rounded sides (or considered as substantially elliptical with two substantially parallel straight sides), and define a place including a major axis "M" and a minor axis "N." The passageway can also be of other shapes.

In the open configuration (FIGS. 4 and 5), the leading ends 110c, 120c are in substantially spaced relation across the major axis "M" at spaced positions along minor axis "N" as they form outer ends of the device 100. The trailing ends 110d, 120d are in substantial abutting mirrored relation across the major axis "M" and at close proximal positions along minor axis "N" as the inner edges are adjacent. Also in the open configuration, the leading ends 110c, 120c and the trailing ends 110d, 120d are substantially in the same plane, e.g., substantially similarly longitudinally positioned along longitudinal axis "L." In the closed configuration (FIG. 6), the leading ends 110c, 120c and the trailing ends 110d, 120d are in closer proximity and preferably in substantial abutting relation across the major axis "M" and in close proximal positions along minor axis "N." In addition, the leading ends 110c, 120c are at spaced longitudinal positions relative to the trailing ends 110d, 120d along the longitudinal axis "L" in the closed configuration. Thus, as can be appreciated leading ends 110c, 120c are on the exterior sides of the access device 100 in the open configuration shown in FIG. 4 and are moved adjacent one another in the closed configuration of FIG. 6.

With continued reference to FIG. 4, the first member 110 may include one or more flaps 112 extending into the passage 130 and the second member 120 may include one or more flaps 122 extending into the passage 130. The flaps 112, 122 may be positioned relative adjacent ribs "R" (FIG. 3). Note that during the surgical procedure, surgical tools might be inserted through the access port and torque applied can result in pressure on and damage to tissues including nerves running along the ribs. The flaps 112, 122 are designed to spread point loads and thus reduce such trauma to the tissue during the procedure.

Referring again to FIGS. 4-6, in the open configuration, the leading ends 110c, 120c of the first and second members 110, 120 are diametrically opposed and the top and the bottom surfaces 110a, 110b of the first member 110 are substantially aligned with the top and bottom surfaces 120a, 120b of the second member 120 along an axis substantially transverse to a central axis "X" defined through the passage 130. As best shown in FIG. 5, the central axis "X" may be substantially aligned with a longitudinal axis "L" of the insertion device 200. The trailing ends 110d, 120d are positioned in close cooperative alignment when the first and second members 110, 120 are in the open configuration. In the closed (e.g. folded or collapsed) configuration, the leading and trailing ends 110c, 110d of the first member 110 are substantially aligned with the leading and trailing ends 120c, 120d of the second member 120 and the bottom surfaces 110b, 120b of the first and second members 110, 120 are disposed in substantially mirrored relation. The top surfaces 110a, 120d are positioned in close cooperative alignment when the first and second members 110, 120 are in the closed configuration. That is, as the device 10 is folded, the top surfaces 110a, 120d are folded toward each other to the position of FIG. 6, where the leading ends 110c, 120c are moved adjacent one another. Bottom surfaces 120, 120b then form the outer sides of the device 100.

With continued reference to FIG. 4, the first member 110 defines one or more apertures 114 and the second member 120 defines one or more apertures 124. The apertures 114, 124 are dimensioned to facilitate the positioning of the first and the second members 110, 120 into the open configuration. The aperture 114 includes a first portion 114a and a second portion 114b. Similarly, the aperture 124 includes a first portion 124a and a second portion 124b. The first portions 114a, 124a are smaller than the second portions 114b, 126a.

The first member 110 includes a surface feature 116 defined therealong. The surface feature 116 may include one or more tapered portions 116a. Similarly, the second member 120 includes a surface feature 126 defined therealong. The surface feature 126 may include one or more tapered portions 126a. The surface features 116, 126 are in contact with each other when the first and second members 110, 120 are in the closed configuration. The tapered portions 116a, 126a of the first and second members 110, 120 may have complementary mating surfaces with at least a portion of the surface feature 116, 126 of the other respective member 110, 120. In this manner, the tapered portions 116a, 126 enable the surface features 116, 126 to engage each other in close cooperative alignment.

Figure 7:
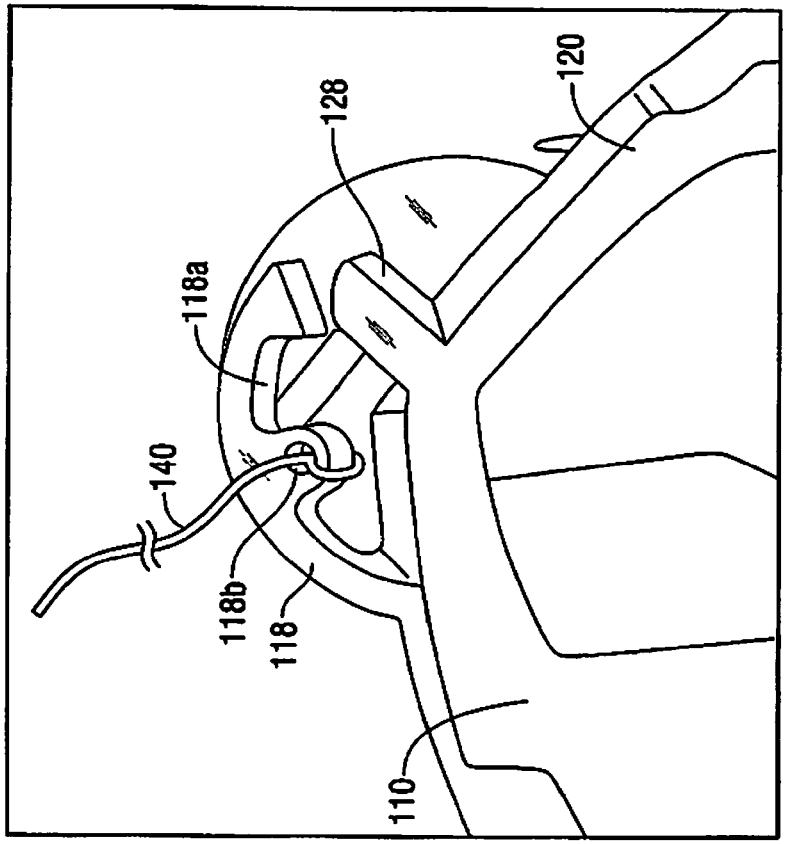
FIG. 7 is an enlarged, partial perspective view of the surgical access device of FIG. 4 shown disposed between open and closed configurations.

As best shown in FIG. 7, a first arm 118 extends from the first member 110. A second arm 128 extends from the second member 120. The first arm 118 defines a channel 118a dimensioned to receive the second arm 128 such that the first arm 118 and the second arm 128 are engaged in close geometric fit when the first and second members 110, 120 are positioned in the open configuration so that the first and second members 110, 120 are secured in the open configuration. One or more cords 140 may be secured to one or both of the first arm 118 and the second arm 128. When the first and second members 110, 120 are secured in the open configuration, the one or more cords 140 are actuable, upon the application of a predetermined amount of force, to disengage the first and second arms 118, 128 from the close geometric fit so that the first and second members 110, 120 are no longer secured in the open configuration. An opening 118b may be defined within one or more of the first arm 118 and the second arm 128 through which the one or more cords 140 may be secured.

Referring now to FIGS. 8-12, the insertion device 200, which may be disposable, includes a housing 202 having a shaft 204 extending from the housing 202 and a movable assembly 210 at a distal end of shaft 204. A lumen 201 is defined through the housing 202 and the shaft 204. One or more movable elements 210a, 210b extend from a distal end of the shaft 204 and are pivotally coupled to the distal end thereof via pins 203. In particular, first and second movable elements 210a, 210b may be secured on opposed ends of the distal end of the shaft 204 via pins 203a, 203b so that they pivot in opposite directions. An actuator 206 is operably coupled to the movable elements 210a, 210b and is operable to move the movable elements 210a, 210b between first and second positions. As best illustrated in FIG. 9, the distal end of the actuator 206 may be pivotally connected via pin 203c to extensions 211 extending from each respective movable element 210a, 210b. Extension 211a of first movable element 210d enables the first movable element 210d to rotate about both pins 203a and pin 203c when the actuator 206 is longitudinally translated. Similarly, the extension (not shown but identical to extension 211a and disposed on the opposed side in substantially mirrored relation) of second movable element 210b enables the second movable element 210b to rotate about both pins 203b and pin 203c when the actuator 206 is longitudinally translated. In this respect, each of the extensions 211 of the first and second movable elements 210a, 210b pivots and longitudinally translates, simultaneously, in response to the longitudinal actuation of the actuator 206. In addition, both the extensions 211 of the first and second movable elements 210a, 210b also simultaneously longitudinally translate with respect to each other; however, each movable element 210a, 210b pivots in opposed direction about pin 203c with respect to the other, as discussed above. Specifically, movable elements 210a, 210b pivot away from one another when being positioned in an open configuration and away from one another when being positioned in a closed configuration.

Referring now to FIGS. 4 and 10-12, the movable elements 210a, 210b are substantially aligned with a longitudinal axis "L" of the insertion device 200 in the first position and substantially aligned with an axis "Z" that is transverse to the longitudinal axis "L" of the insertion device 200 in the second position. The movable elements 210a, 210b of the insertion device 200 are releaseably engagable with one or both of the first and second members 110, 120 of the surgical access device 100 such that movement of the movable elements 210a, 210b between the first and second positions repositions the first and second members 110, 120 of the surgical access device 100 between open and closed configurations when the movable elements 210a, 210b) are engaged with one or both of the first and second members 110, 120 of the surgical access device 100. As best shown in FIG. 5, when the movable elements 210a, 210b are positioned in the second position, the movable elements 210a, 210b are prevented from crossing the plane defined by the substantially elliptical passage 130 of the surgical access device 100 when the movable elements 210a, 210b are not substantially aligned with the major axis "M" (FIG. 4) defined by the substantially elliptical passage 130 of the surgical access device 100.

With reference to FIGS. 4-5, the movable elements 210a, 210b of the insertion device 200 include one or more protuberances 212 extending therefrom. The apertures 114, 124 of the surgical access device 100 and the protuberances 212 of the insertion device 200 are engagable. The protuberances 212 are dimensioned to engage the smaller first portions 114a, 124a of the apertures 114, 124 in a tight geometric fit and the larger second portions 114b, 124b in a loose geometric fit such that the one or more protuberances 212 remain substantially secured to the first portions 114a, 124a of the apertures 114, 124 when engaged therewith and are substantially freely movable relative to the second portions 114b, 124b of the apertures 114, 124 when engaged therewith.

With reference now to FIGS. 13-17, an alternative embodiment of the presently disclosed surgical access device will be discussed. The embodiment disclosed herein below is similar to the surgical access device 100 discussed above, and accordingly, will only be discussed to the extent necessary to describe the differences in structure and operation thereof.

Figure 13:
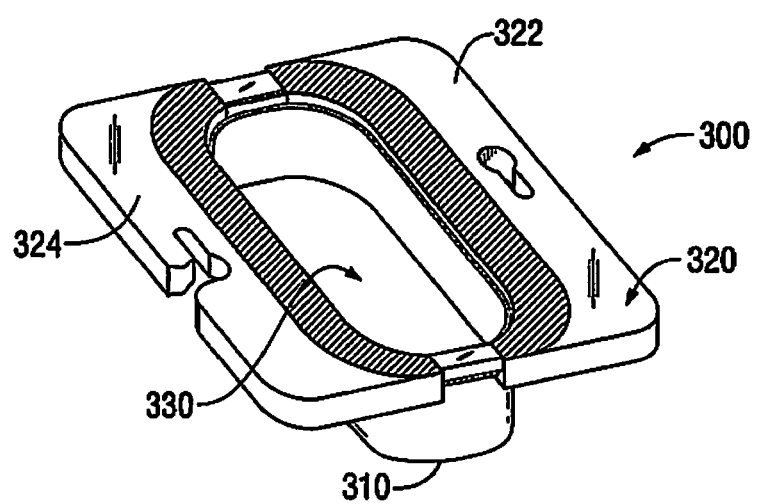
FIG. 13 is a perspective view of another embodiment of the surgical access device in accordance with the present disclosure.

FIG. 13 illustrates an embodiment of the presently disclosed surgical access device that is identified by the reference numeral 300. The surgical access device 300 includes a base 310 and a body 320 operably couplable to the base 310. As best shown in FIG. 14, the base 310 includes a support 312, a first wing 314a, and a second wing 314b. The first and second wings 314a, 314b are substantially identical and are secured to opposite ends of the support 312. The first and second wings 314a, 314b each include a planar surface 315 on which the body 320 is positioned. The support 312 defines a passage 312a that is substantially elliptical and defines a major axis "M" and a minor axis "N." The first and second wings 314a, 314b each include first and second elements 316a, 316b. The first and second elements 316a, 316b are pivotable between a folded condition, where the first and second elements 316a, 316b are substantially aligned with a central axis "C" defined through the passage 312a, and an unfolded condition, where the first and second elements 316a, 316b are substantially aligned with minor axis "N," which is transverse to the central axis "C." The first and second elements 316a, 316b each define a contoured surface 318a, 318b. The contoured surfaces 318a, 318b are dimensioned to engage complimentary mating surfaces (not shown) defined on the bottom surface of the body 320 of the surgical access device 300 such that pivoting, e.g. folding, of the first and second elements 316a, 316b folds the connected body 320 as described below.

Referring now to FIG. 15, the body 320 includes a first member 322 and a second member 324. The first member 322 includes a top surface 322a, a bottom surface 322b, a leading end 322c, and a trailing end 322d. The second member 324 includes a top surface 324a, a bottom surface 324b, a leading end 324c, and a trailing end 324d. The first and second members 322, 324 are each movable between (open) unfolded (FIG. 17) and (closed) folded (FIG. 16) configurations and are positionable within the opening in tissue to provide access to the intercostal space "T" (FIG. 3) defined between a patient's adjacent ribs "R." One or both of the first and second members 322, 324 may rotate as the first and second members 322, 324 move between the unfolded and folded configurations. As illustrated in FIGS. 16-17, each of the first and second members 322, 324 are shown rotating about 90 degrees between the unfolded and folded configurations, although other degrees of rotation are also contemplated. As best shown in FIG. 13, the first and second members 322, 324 define a passage 330 therethrough when positioned in the unfolded configuration. The passage 330 is substantially aligned with the passage 312a when the first and second members 322, 324 are in the unfolded configuration so that passages 312a and 330 are dimensioned to permit access to the intercostal space "T" (FIG. 3) for passage of one or more surgical instruments into an internal work site. Each passage 312a and 330 may be substantially rectangular with rounded ends and define a plane including a major axis "M" and a minor axis "N." Each of the passages 312a, 330 are substantially similar to passage 130 discussed above. Other shapes of the passage are also contemplated.

The access device 300 can be composed of several components to facilitate the use of different material properties in different areas of the device 300. Since the base 310 is designed to flex it can be made of a material such as polypropylene. Since body 320 is attached, e.g. welded or bonded, to a membrane, it is composed of a material that is compatible with the material of the membrane. It is also envisioned that various molding techniques can be utilized to manufacture device 300 to allow different materials to be used in different regions of a component.

In the open configuration (FIG. 17), the leading ends (or outer ends) 322c, 324c are in substantially spaced relation across the major axis "M" at spaced positions along minor axis "N" and the trailing ends (or inner ends) 322d, 324d are in adjacent (or in some embodiments abutting) mirrored relation across the major axis "M" and at close proximal positions along minor axis "N." Also, in the open configuration, the leading ends 322c, 324c and the trailing ends 322d, 324d are substantially in the same plane, e.g., substantially similarly longitudinally positioned along longitudinal axis "L." In the closed configuration (FIG. 16), the leading ends 322c, 324c and the trailing ends 322d, 324d are in substantial mirrored relation across the major axis "M" and in close proximal positions along minor axis "N." In addition, the leading ends 322c, 324c are at spaced longitudinal positions relative to the trailing ends 322d, 324d along the longitudinal axis "L" in the closed configuration.

Figure 18:
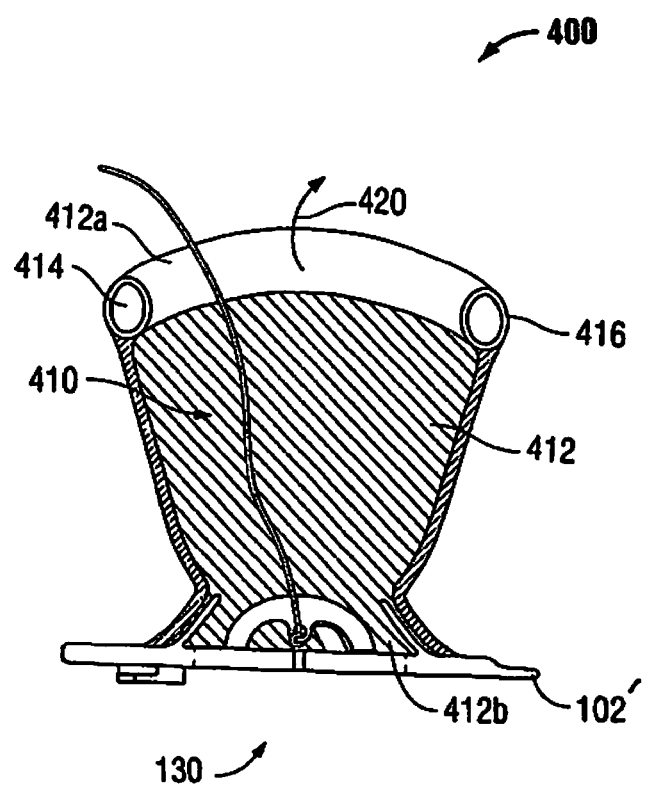
FIG. 18 is a front, perspective view, in partial cross-section of another embodiment of the surgical access device in accordance with the present disclosure.

With reference now to FIG. 18, another alternative embodiment of the presently disclosed surgical access device will be discussed. The embodiment disclosed herein below is similar to the surgical access device 100 discussed above, and accordingly, will only be discussed to the extent necessary to describe the differences in structure and operation thereof.

FIG. 18 illustrates another embodiment of the presently disclosed surgical access device that is identified by the reference numeral 400. Surgical access device 400 includes a membrane assembly 410 extending from body 102', which is identical to body 102 of FIG. 1 (except for the membrane attachment). Body 102' can be inserted into the patient using the insertion device 200 in the same manner body 102 is inserted. The membrane assembly includes a flexible membrane 412 and a ring 414. The flexible membrane 412 includes proximal and distal ends 412a, 412b. The distal end 412b of the flexible member 412 may be coupled to and extend proximally from the internally positioned body 102 of the surgical access device 400. The flexible membrane 412 is generally funnel shaped and protects and isolates tissue surrounding the surgical access device 400 from the passage 130 extending therethrough, thus reducing the risk of tissue damage and/or infection during the surgical procedure. The flexible membrane 412 may be configured for soft tissue retraction and may be of sufficient elasticity to permit retraction of a wide range of tissue thicknesses since there may be a wide range of tissue thicknesses among different patients. Furthermore, the flexible membrane 412 is formed of a material of sufficient strength to prevent accidental tearing and/or puncture by surgical instrumentation inserted through the surgical access device 400. Additionally, the flexible membrane 412 may be made from a bio-compatible material to reduce the incidents of adverse reaction by a patient upon contact with the patient's tissue. Flexible membrane 412 may also be made of a transparent material to allow the surgeon to better visualize the surgical site and surrounding tissue.

The continuous ring 414 is coupled to the proximal end 412a of flexible membrane 412 outside the patient. Ring 414 may be disposed through a loop 416 formed at the proximal end 412a of flexible membrane 412. Proximal end 412a of flexible membrane 412 may be folded back onto and adhered to flexible membrane 412 to define loop 416 therebetween, or, alternatively, proximal end 412a of flexible membrane 412 may be engaged to ring 414 via any other suitable mechanism. Ring 414 may be made from a flexible or a semi-rigid material. The ring 414 may be sufficiently rigid to retain membrane 412 in an open, tensioned configuration, while being somewhat flexible such that ring 414 may be rotated about a circumference thereof to roll, or wind-up flexible membrane 412 therearound, as shown by arrows 420. Thus, as ring 414 is rotated in the direction of arrows 420, membrane 412 is rolled-up around ring 414 and tensioned, thereby flexing the surgical access device 400 further outwardly to retract tissue and/or to expand the passage 130 extending through the surgical access device 400.

With continued reference to FIGS. 1-18, use and operation of the presently disclosed surgical access assembly 10 will be discussed during the course of a minimally invasive surgical procedure. While the surgical access assembly 10 will be discussed in the context of a thoracic procedure, it should be appreciated that the following discussion of the surgical access assembly 10 is applicable to other minimally invasive surgical procedures.

Initially, the opening is made in the outer tissue wall of the thoracic cavity "T" (FIG. 3). Thereafter, if not already having been coupled to one of the presently disclosed surgical access devices, the insertion device 200 is coupled thereto. As best shown in FIG. 5, the movable elements 210a, 210b of the insertion device 200 are coupled to one or both of the first and second members of one of the presently disclosed surgical access devices. In this manner, the protuberances 212 of the movable elements 210a, 210b are positioned within the larger second portions 114b, 124b of the apertures 114, 124. Then, the movable elements 210a, 210b of the insertion device 200 are rotated so that the protuberances 212 couple with the smaller first portions 114a, 124a in close geometric fit, whereby the protuberances 212 are substantially secured to the first portions 114a, 124a. As such, the insertion device 200 is enabled to reposition the surgical access device between open (FIGS. 2, 13 and 17) and closed (FIGS. 1, 6 and 16) configurations upon the actuation (e.g., longitudinal translation) of the actuator 206. In the closed configuration, the surgical access device is in an approximated position such that the surgical access device assumes a reduced profile defining a smaller transverse dimension than in the open configuration. The reduced transverse dimension facilitates atraumatic insertion and removal of the surgical access device.

With the insertion device 200 maintaining the surgical access device in the closed configuration (FIGS. 1 and 6), the clinician, with the insertion device 200, inserts the surgical access device into the opening and positions the surgical access device in the intercostal space between adjacent ribs "R" into desired placement for providing the clinician access to the thoracic cavity "T" (FIG. 3). Specifically, the insertion device 200, with reference to FIGS. 10-12, is actuated via the actuator 206 in order to reposition the surgical access device into the open position so that the surgical access device may be positioned between adjacent ribs "R."

Figure 10:
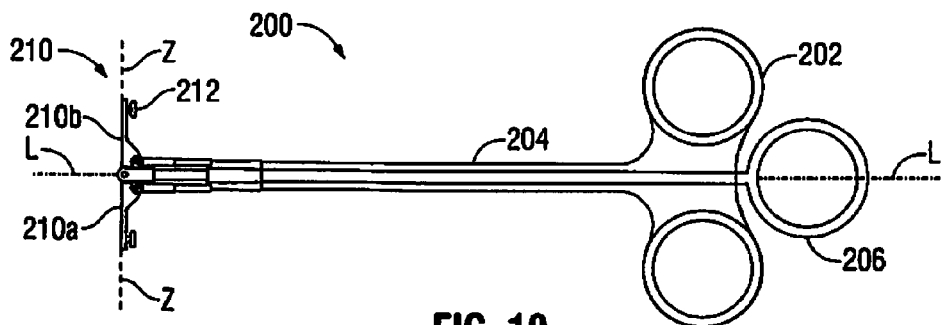
FIGS. 10-12 are progressive views of the insertion device of the presently disclosed surgical access assemblies showing the insertion device being repositioned between open and closed configurations.
Figure 11:
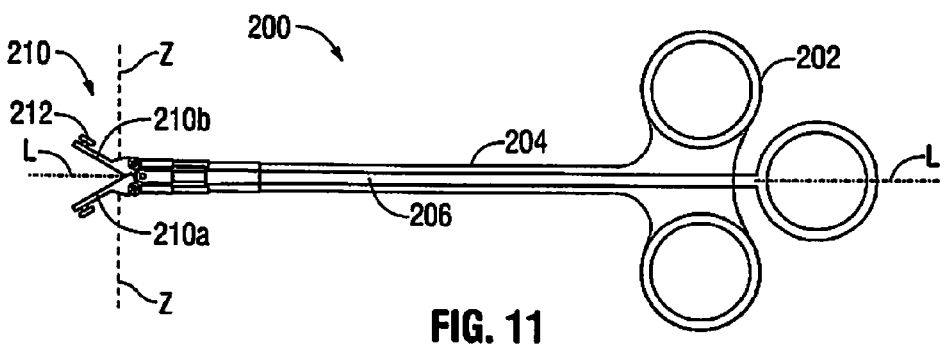
Figure 12:
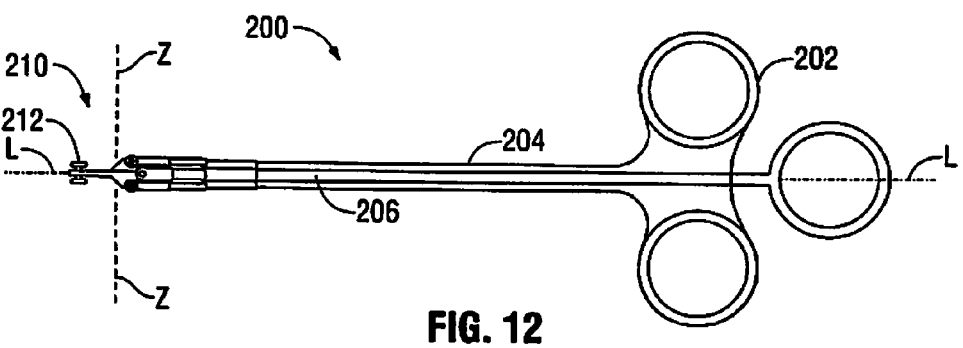

With continued reference to FIGS. 10-12, when actuation is desired, the clinician translates the actuator 206 in the distal direction. The actuator 206 longitudinally translates so that each movable element 210a, 210b moves from the closed configuration to the open configuration, whereby the surgical access device coupled thereto also moves from the closed configuration to the open configuration. In order to secure the surgical access device in the open configuration, the actuator 206 is translated to a distal-most position. With particular regard to surgical access device 100, the first and second arms 118, 128 of the first and second members 110, 120 engage in close geometric fit in order to maintain the surgical access device 100 in the open configuration when positioned between the adjacent ribs "R."

Referring now to FIG. 18, in embodiments that include the membrane assembly 410, the flexible membrane 412 may be positioned proximally of the opening so that it protects and isolates the surrounding tissue. In addition, the flexible membrane 412 may be tensioned, e.g., via the ring 414, by pulling the ring 414 or rotating the membrane 412 about the ring 414, to realize the desired positioning. In some embodiments, the ring 414 can be expandable by sliding first and second ring components away from each other to tension the membrane.

With reference again to FIG. 5, the insertion device 200 may then be uncoupled from surgical access device in order to permit removal of the insertion device 200. In particular, the one or more movable elements 210a, 210b are rotated so that the protuberances 212 move into the second portions 114b, 124b, thereby enabling the movable elements 210a, 210b to be uncoupled.

After uncoupling the movable elements 210a, 210b of the insertion device 200 from the surgical access device, the insertion device 200 can then be repositioned into the closed configuration upon the proximal translation of the actuator 206 (FIG. 12). In the closed configuration, the insertion device 200 assumes a reduced profile defining a smaller transverse dimension than in the open configuration. The reduced transverse dimension facilitates atraumatic insertion and removal of the insertion device 200. Once positioned in the closed configuration, the insertion device 200 may be atraumatically removed through the passage of one of the presently disclosed surgical access devices.

After removal of the insertion device 200, the clinician carries out the remainder of the surgical procedure by passing one or more surgical instruments through the passage of one of the presently disclosed surgical access devices. However, it should be appreciated that some instruments may be passed through the passage while the insertion device 200 is coupled to the surgical access device.

The surgical instrument(s) inserted through one of the presently disclosed surgical access devices may be any surgical instrument(s) configured and dimensioned to pass through one of the passages of the presently disclosed surgical access devices, and adapted to perform a surgical, diagnostic, or other desired procedure. For example, suitable surgical instruments may include an endoscopic apparatus, which perform a variety of functions such as the application of surgical clips or other such fasteners, the cutting of body tissue, and/or specimen retrieval for removing an internal tissue sample.

In order to facilitate passage of the surgical instrument(s) into the thoracic cavity "T," and/or removal of the surgical instrument(s) therefrom, it is envisioned that surgical instrument(s), and or the insertion device 200, and/or any of the presently disclosed surgical access devices, may be partially, or entirely, coated with a biocompatible, lubricous material.

Following completed use of the surgical instrument(s), the instrument(s) are withdrawn from the surgical access device. The surgical access device may then be returned to the closed configuration, via reinsertion and coupling of the insertion device 200 as described above. After coupling the insertion device 200 to the surgical access device as described above, the actuator 206 is then proximally translated so that one or more movable elements 210a, 210b reposition the surgical access device into the closed configuration for facilitating removal of the surgical access device from between the adjacent ribs "R." In this respect, the reduced profile of the surgical access device in the closed configuration allows for atraumatic removal of the surgical access device from the intercostal space "S."

Alternatively, the surgical access device may be repositioned into the closed configuration for removal upon the application of a predetermined amount of force to the one or more cords 140 as best illustrated in FIG. 7. The one or more cords 140 impart a force upon the surgical access device that enables the surgical access device to approximate the closed configuration for facilitating removal of the surgical access device from the intercostal space "S." With particular regard to the surgical access device 100, the predetermined force causes the first and second arms 118, 128 to become disengaged, thereby enabling the first and second members 110, 120 to be repositioned such that they approximate towards the closed configuration for facilitating removal of the surgical access assembly 100 from between the adjacent ribs "R." In this respect, the reduced profile of the surgical access device 100 in the closed configuration allows for atraumatic removal of the surgical access device 100 from the intercostal space "S."

Persons skilled in the art will understand that the structures and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical access system comprising,
a surgical access device including a body having a first member and a second member, the first member being movable with respect to the second member between open and closed configurations, and each of the first member and the second member being positionable at least partially within an opening in tissue to provide access to an internal space of a patient, wherein in the open configuration the first member and the second member define a passage therebetween, the passage being dimensioned to permit access of a surgical instrument to the internal space; and
an insertion device including a housing having a shaft extending from the housing a first movable element pivotally coupled to a distal portion of the shaft, a second movable element pivotally coupled to a distal portion of the shaft, and an actuator operably coupled to the first movable element and operable to move the first movable element between first and second positions;
wherein the first movable element of the insertion device is releasable engageable with at least one of the first member or the second member such that movement of the first movable element between the first and second positions moves the first member between open and closed configurations when the first movable element is engaged with at least one of the first member or the second member;
wherein at least one of the first movable element or the second movable element is substantially aligned with a longitudinal axis defined by the shaft of the insertion device in the first position, and substantially aligned with an axis transverse to the longitudinal axis in the second position.

2. The surgical access system according to claim 1, wherein each of the first member and the second member includes a top surface, a bottom surface, a leading end, and a trailing end, the top surface of the first member being positioned in close cooperative alignment to the top surface of the second member when the first member and the second member are in the closed configuration, the trailing end of the first member being positioned in close cooperative alignment to the trailing end of the second member when the first member and the second member are in the open configuration and in the closed configuration.

3. The surgical access system according to claim 2, wherein each of the first member and the second member includes a tapered portion defined along the top surface thereof, each respective tapered portion being in contact with the other tapered portion when the first member and the second member are in the closed configuration.

4. The surgical access system according to claim 2, wherein in the open configuration, the leading end of the first member and the leading end of the second member are diametrically opposed, and wherein the top surface and the bottom surface of the first member are substantially aligned with the top surface and the bottom surface of the second member along an axis transverse to a central axis defined through the passage.

5. The surgical access system according to claim 4, wherein in the closed configuration, the leading end and the trailing end of the first member are substantially aligned with the leading end and the trailing end of the second member, and the bottom surface of the first member is disposed in a substantially mirrored relation with respect to the bottom surface of the second member.

6. The surgical access system according to claim 1, wherein at least one of the first member or the second member defines at least one aperture, and wherein at least one of the first movable element or the second movable element of the insertion device includes at least one protuberance extending therefrom, the at least one protuberance being engageable with the at least one aperture.

7. The surgical access system according to claim 6, wherein the at least one aperture includes a larger portion and a smaller portion, and wherein the at least one protuberance is dimensioned to engage the smaller portion in a tight geometric fit and is dimensioned to engage the larger portion in a loose geometric fit such that the at least one protuberance remains substantially secured to the smaller portion when engaged therewith and is substantially freely movable relative to the larger portion when engaged therewith.

8. The surgical access system according to claim 1, wherein the passage defined between the first member and the second member in the open configuration is substantially elliptical.

9. The surgical access system according to claim 1, wherein each of the first movable element and the second movable element is pivotable with respect to the actuator.

10. The surgical access system according to claim 1, wherein the first member includes a first arm extending therefrom, the second member includes a second arm extending therefrom, the first arm defining a channel therein, the channel dimensioned to receive the second arm such that the first arm and the second arm are engaged in close geometric fit when the first member and the second member are positioned in the open configuration so that the first member and the second member are secured in the open configuration.

11. The surgical access system according to claim 10, further comprising at least one cord secured to at least one of the first arm and the second arm, wherein when the first member and the second member are secured in the open configuration, the at least one cord is actuatable upon the application of a predetermined amount of force to disengage the first arm and the second arm from the close geometric fit so that the first member and the second member are no longer secured in the open configuration.

12. The surgical access system according to claim 11, wherein at least one of the first arm and the second arm defines an opening therethrough, and wherein the at least one cord passes through the opening.

13. The surgical access system according to claim 1, wherein the first member includes at least one flap extending toward the second member when the first member and the second member are in the open configuration.

14. The surgical access system according to claim 1, wherein each of the first member and the second member rotates about 90 degrees relative to a central axis defined through the passage as the first member and the second member move between the open and closed configurations.

15. A surgical access system comprising,
a surgical access device including a body having a first member and a second member, the first member being movable with respect to the second member between open and closed configurations, and each of the first member and the second member being positionable at least partially within an opening in tissue to provide access to an internal space of a patient, wherein in the open configuration the first member and the second member define a passage therebetween, the passage being dimensioned to permit access of a surgical instrument to the internal space; and
an insertion device including a housing having a shaft extending from the housing, at least one movable element disposed adjacent a distal end of the shaft, and an actuator operably coupled to the at least one movable element and operable to move the at least one movable element between first and second positions;
wherein the at least one movable element of the insertion device is releasably engageable with at least one of the first member or the second member such that movement of the at least one movable element between the first and second positions moves the first member between open and closed configurations when the at least one movable element is engaged with at least one of the first member or the second member;
wherein at least one of the first member or the second member defines at least one aperture, and wherein the at least one movable element of the insertion device includes at least one protuberance extending therefrom, the at least one protuberance being engageable with the at least one aperture;
wherein the at least one aperture includes a larger portion and a smaller portion, and wherein the at least one protuberance is dimensioned to engage the smaller portion in a tight geometric fit and is dimensioned to engage the larger portion in a loose geometric fit such that the at least one protuberance remains substantially secured to the smaller portion when engaged therewith and is substantially freely movable relative to the larger portion when engaged therewith.

16. The surgical access system according to claim 15, wherein each of the first member and the second member includes a top surface, a bottom surface, a leading end, and a trailing end, the top surface of the first member being positioned in close cooperative alignment to the top surface of the second member when the first member and the second member are in the closed configuration, the trailing end of the first member being positioned in close cooperative alignment to the trailing end of the second member when the first member and the second member are in the open configuration and in the closed configuration.

17. A surgical access system comprising,
a surgical access device including a body having a first member and a second member, the first member being movable with respect to the second member between open and closed configurations, and each of the first member and the second member being positionable at least partially within an opening in tissue to provide access to an internal space of a patient, wherein in the open configuration the first member and the second member define a passage therebetween, the passage being dimensioned to permit access of a surgical instrument to the internal space; and
an insertion device including a housing having a shaft extending from the housing a first movable element pivotally coupled to a distal portion of the shaft, a second movable element pivotally coupled to a distal portion of the shaft, and an actuator operably coupled to the first movable element and operable to move the first movable element between first and second positions;
wherein the first movable element of the insertion device is releasably engageable with at least one of the first member or the second member such that movement of the first movable element between the first and second positions moves the first member between open and closed configurations when the first movable element is engaged with at least one of the first member or the second member;
wherein at least one of the first member or the second member defines at least one aperture, and wherein at least one of the first movable element or the second movable element of the insertion device includes at least one protuberance extending therefrom, the at least one protuberance being engageable with the at least one aperture;
wherein the at least one aperture includes a larger portion and a smaller portion, and wherein the at least one protuberance is dimensioned to engage the smaller portion in a tight geometric fit and is dimensioned to engage the larger portion in a loose geometric fit such that the at least one protuberance remains substantially secured to the smaller portion when engaged therewith and is substantially freely movable relative to the larger portion when engaged therewith.

18. A surgical access system comprising,
a surgical access device including a body having a first member and a second member, the first member being movable with respect to the second member between open and closed configurations, and each of the first member and the second member being positionable at least partially within an opening in tissue to provide access to an internal space of a patient, wherein in the open configuration the first member and the second member define a passage therebetween, the passage being dimensioned to permit access of a surgical instrument to the internal space; and an insertion device including a housing having a shaft extending from the housing a first movable element pivotally coupled to a distal portion of the shaft, a second movable element pivotally coupled to a distal portion of the shaft, and an actuator operably coupled to the first movable element and operable to move the first movable element between first and second positions;

wherein the first movable element of the insertion device is releasably engageable with at least one of the first member or the second member such that movement of the first movable element between the first and second positions moves the first member between open and closed configurations when the first movable element is engaged with at least one of the first member or the second member;

wherein each of the first member and the second member rotates about 90 degrees relative to a central axis defined through the passage as the first member and the second member move between the open and closed configurations.

* * * * *